US011155878B2

(12) United States Patent
Ridder et al.

(10) Patent No.: US 11,155,878 B2
(45) Date of Patent: *Oct. 26, 2021

(54) METHOD FOR DISCRIMINATION OF METAPLASIAS FROM NEOPLASTIC OR PRENEOPLASTIC LESIONS

(71) Applicant: Ventana Medical Systems, Inc., Tucson, AZ (US)

(72) Inventors: Ruediger Ridder, Schriesheim (DE); Magnus Von Knebel Doeberitz, Heidelberg (DE); Peter Martin, Gaiberg (DE)

(73) Assignee: Ventana Medical Systems, Inc., Tucson, AZ (US)

( * ) Notice: Subject to any disclaimer, the term of this patent is extended or adjusted under 35 U.S.C. 154(b) by 77 days.

This patent is subject to a terminal disclaimer.

(21) Appl. No.: 16/279,900

(22) Filed: Feb. 19, 2019

(65) Prior Publication Data

US 2019/0177804 A1  Jun. 13, 2019

Related U.S. Application Data

(63) Continuation of application No. 15/479,961, filed on Apr. 5, 2017, now Pat. No. 10,246,751, which is a continuation of application No. 14/325,282, filed on Jul. 7, 2014, now Pat. No. 10,822,660, which is a continuation of application No. 13/137,547, filed on Aug. 25, 2011, now Pat. No. 8,815,520, which is a continuation of application No. 12/164,934, filed on Jun. 30, 2008, now Pat. No. 8,043,819, which is a continuation of application No. 10/511,108, filed as application No. PCT/EP03/50096 on Apr. 8, 2003, now Pat. No. 7,422,859.

(30) Foreign Application Priority Data

Apr. 9, 2002 (EP) .................................... 02007954

(51) Int. Cl.
*C12Q 1/6886* (2018.01)
*C12Q 1/70* (2006.01)
*G01N 33/574* (2006.01)

(52) U.S. Cl.
CPC ........... *C12Q 1/6886* (2013.01); *C12Q 1/708* (2013.01); *G01N 33/57411* (2013.01); *C12Q 2600/112* (2013.01); *C12Q 2600/158* (2013.01); *G01N 2333/025* (2013.01)

(58) Field of Classification Search
CPC .................................................... C12Q 1/6886
USPC ......................................................... 435/6.1
See application file for complete search history.

(56) References Cited

U.S. PATENT DOCUMENTS 7,056,690 B2 * 6/2006 Laskey ............ G01N 33/57484
435/7.23
2002/0106685 A1* 8/2002 Henning .......... G01N 33/57411
435/6.14

OTHER PUBLICATIONS

Solomon et al. (2001, J. of the National Cancer Institute 93(4):293-299).*
Klaes et al. (2001, Int. J. Cancer 92:276-284).*
Guccione (Virology 293:20-25 (2002).*
Khan et al (Journal of Virology, Jun. 1993, 67(6): 3396-3403).*
Von Knebel Doeberitz (2001, Dis. Markers 17(3):123-128).*
Gravitt et al (Cancer Epidemiology, Biomarkers, and Prevention, 2001, 10: 95-100).*
Pantel et al (Journal of Hematotherapy, 1994, 3: 165-173).*

* cited by examiner

*Primary Examiner* — Sean E Aeder
(74) *Attorney, Agent, or Firm* — Ventana Medical Systems, Inc.

(57) ABSTRACT

The present invention relates to a method for discrimination of $p16^{INK4a}$ overexpressing metaplasias from neoplastic or preneoplastic $p16^{INK4a}$ overexpressing lesions by determination of the level of high risk HPV encoded gene-products such as e.g. HPV E2 and/or HPV E7 molecules in biological samples in the course of cytological testing procedures. The method thus enables for reduction of false positive results in the $p16^{INK4a}$ based detection of anogenital lesions in cytological testing procedures.

17 Claims, 6 Drawing Sheets

METHOD FOR DISCRIMINATION OF METAPLASIAS FROM NEOPLASTIC OR PRENEOPLASTIC LESIONS

This application is a continuation of U.S. application Ser. No. 15/479,961, filed Apr. 5, 2017; which is a continuation of U.S. application Ser. No. 14/325,282, filed Jul. 7, 2014; which is a continuation of U.S. application Ser. No. 13/137,547, filed Aug. 25, 2011, now U.S. Pat. No. 8,815,520; which is a continuation of U.S. application Ser. No. 12/164,934, filed Jun. 30, 2008, now U.S. Pat. No. 8,043,819; which is a continuation of U.S. application Ser. No. 10/511,108, filed Oct. 8, 2004, now U.S. Pat. No. 7,422,859; which is a National Stage of International Application PCT/EP2003/050096, filed Apr. 8, 2003, published Jan. 15, 2004, under PCT Article 21(2) in English; which claims the priority of European Application No. 02007954.7, filed Apr. 9, 2002. The contents of the above-identified applications are incorporated herein by reference in their entireties.

TECHNICAL FIELD

The present invention relates to a method for discrimination of $p16^{INK4a}$ overexpressing metaplasias from neoplastic or preneoplastic $p16^{INK4a}$ overexpressing lesions by determination of the level of high risk HPV encoded gene-products such as e.g. HPV E2 or E7 molecules in biological samples in the course of cytological testing procedures. The method thus enables for reduction of false positive results in the $p16^{INK4a}$ based detection of anogenital lesions in cytological testing procedures.

BACKGROUND OF THE INVENTION

The detection of the overexpression of $p16^{INK4a}$ in biological samples has proven as a useful marker in the detection of anogenital lesions such as carcinoma of the uterine cervix (see WO00/01845; Klaes et al., Int. J. Cancer: 92, 276-284 (2001)). The method based on $p16^{INK4a}$-specific immuno-chemical staining allows for a sensitive and specific identification of dysplastic cells in tissue section and in cytological samples.

In immuno-histochemical examinations of tissues, neoplastic cells can be stained using a $p16^{INK4a}$ specific antibody mediated staining procedure. The histological diagnosis of neoplastic lesions can thus be supported by a staining based on a molecular marker characteristic for transformation of cells in anogenital lesions. The diagnosis, whether or not cells are neoplastic, in these procedures is not solely based on the $p16^{INK4a}$ specific staining, but does also rely on the histological information.

This is due to the fact, that in about 30% of samples, metaplastic cells show some immunoreactivity with $p16^{INK4a}$ specific antibodies, and thus are stained in the course of the procedures. Yet the staining pattern yielded from these metaplastic cells differs from the pattern, which renders from neoplastic lesions. Metaplastic cells give rise to a patchy or focal staining pattern, whereas neoplastic lesions give rise to diffuse staining pattern. Moreover, the staining intensities of metaplastic cells are predominantly less than that of neoplastic cells.

The common methods used in screening tests for the early detection of neoplasias do not employ histology based tests, but do rather rely on cytological testing procedures. Yet especially in cases, when there is no histological information available concerning the architecture of tissues, such as for example in cytological examinations, testing for $p16^{INK4a}$ overexpression alone may lead to false positive results. This is due to the fact, that the metaplastic cells expressing $p16^{INK4a}$ at detectably elevated levels, may not be differentiated by means of a histological staining patterns.

The percentage of cells showing overexpression of $p16^{INK4a}$ increases in the course of emergence of dysplasias. So in neoplastic or preneoplastic stages, when only a restricted population of neoplastic or preneoplastic cells is present in samples the immunoreactivity of $p16^{INK4a}$ may be weak. This weak immunoreactivity may be of about the level as the level caused by metaplastic cells. In later stages of dysplasias the overall immunoreactivity of $p16^{INK4a}$ is stronger and so neoplastic lesions are easily discernible from metaplasias even in a cytological testing format. This might lead to cases, where the presence of metaplastic cells expressing $p16^{INK4a}$ might be confused with the presence of neoplastic cells, and thus produces a false positive result.

Especially in screening tests, where the detection of early stages of neoplasias is desirable this condition is quite unpleasant. This is especially true, as the $p16^{INK4a}$ based diagnosis has proven to be a valuable tool in histological examinations and the application in cytological based screening procedures would be able to enhance these established procedures.

To reduce false positive results in cytological testing formats and so to further enhance the fidelity of the $p16^{INK4a}$ mediated diagnosis of anogenital lesions, a method for discriminating the metaplasias from neoplastic and dysplastic lesions would be desirable. The problem in the art especially pertains to early stages of neoplasias, when the percentage of cells showing $p16^{INK4a}$ overexpression is still at a level, that might be confused with levels of normally occurring $p16^{INK4a}$ overexpressing proliferating metaplastic cells. Thus, useful means for solving the present problem have to involve parameters, that characterize early stages of neoplasias of the anogenital tract. Any characteristics of dysplasias and/or neoplasias emerging during the progress of tumorigenesis, thus proving as diagnostic tools for high grade dysplasias, and are limited in early stages of tumorigenesis are not suitable for the method according to the present invention.

SUMMARY OF THE INVENTION

A method for the discrimination of metaplasias from neoplastic and preneoplastic lesions is provided within the embodiments claimed according to the present invention.

For supporting the discrimination of metaplasias from neoplastic lesions in testing procedures based on the overexpression of $p16^{INK4a}$, a marker molecule that is expressed in neoplastic and/or preneoplastic cells and tissues and is not expressed in metaplastic cells would be suitable.

E2 of HPV is especially expressed in lower grade CIN lesions and the expression decreases with ascending CIN grades (Stevenson et al., J. Gen. Virol., 81, 1825-32 (2000)). In most invasive carcinomas, no expression of E2 protein is detectable. This may be due to the fact, that parts of the E2 gene are lost during integration of the HPV DNA, into the host genome. Thus in persistent HPV infections having integrated HPV DNA no or low E2 expression may be detected.

Due to these facts E2 protein proves to be a marker for early stages of lesions associated with high risk HPV infections. In contrast, $p16^{INK4a}$ is a marker, which is overexpressed even in early stages of anogenital lesions, the expression level of which increases in the course of progression of dysplastic lesions. The fact that E2 is especially expressed in early stages of neoplasias makes it particularly useful for early detection methods. The high expression level of E2 protein in early stages of HPV infection allows to identify infected cells, before there is an abundant number of copies of the virus present in the tested cells.

The L1 and L2 gene-products are also useful for the method according to the present invention due to their high expression level predominantly in early stages of viral infection before integration has occurred. The expression of these gene-products is also reduced in persistent infection of HPV.

The inventors now have found, that cells expressing high risk HPV gene-products such as HPV E2 may serve to discriminate early neoplastic or dysplastic lesions detectable by $p16^{INK4a}$-specific immuno-chemical staining from metaplasias, which may also comprise cells immunoreactive with $p16^{INK4a}$, in the course of cytological testing procedures.

Cells expressing other HPV encoded gene-products, that are detectable on an expression level as mRNA or polypeptide in neoplastic stages or preneoplastic stages, may also serve for the discrimination of neoplastic and/or preneoplastic lesions from metaplasias overexpressing $p16^{INK4a}$ according to the present invention. Examples of such HPV encoded gene-products include HPV E6, E7, L1 or L2 proteins or mRNA.

BRIEF DESCRIPTION OF THE DRAWINGS

For experimental details see Example 1; the cells clearly react with the antibodies against $p16^{INK4a}$.

For experimental details see Example 1; the cells do not show immunoreactivity with the polyclonal antibodies directed against HPV E2 protein.

For experimental details see Example 1; the cells do not show immunoreactivity with the polyclonal antibodies directed against HPV L1 protein.

DETAILED DESCRIPTION OF THE INVENTION

The present invention relates to a method for discrimination of neoplastic, preneoplastic and/or dysplastic lesions from metaplasias comprising $p16^{INK4a}$ overexpressing cells, in biological samples in a cytological testing procedure based on the detection of the presence or absence of cells expressing high risk HPV gene-products in said biological samples. HPV gene-products useful for the method disclosed herein are gene-products, which are highly expressed especially in early stages of neoplastic and preneoplastic lesions. In one embodiment of the invention HPV E2 protein or mRNA may serve as a marker for discrimination of metaplasias from early neoplastic or preneoplastic lesions in samples. Furthermore HPV E6, E7, L1 or L2 protein and/or mRNA also proved to be suitable for performing the discrimination according to the invention disclosed herein.

Discrimination as used in the context of the present invention shall comprise an assessment whether a sample is to be classified in one or another way. In a preferred embodiment of the invention the discrimination pertains to the assessment of a tissue or components thereof being neoplastic or being metaplastic. Thus the discrimination as used herein is a judgement about the growth properties of cells in a sample.

The discrimination according to the present invention is based on the presence or absence of cells expressing a high risk HPV gene-product and on the presence or absence of cells overexpressing $p16^{INK4a}$ in said sample. The cells expressing the high risk HPV gene-products such as E2 need not be the same cells as those overexpressing $p16^{INK4a}$ although the expression of both marker molecules may occur in the same cells.

Thus the presence of cells expressing E2 gene-products in a sample simultaneously with the presence of cells overexpressing $p16^{INK4a}$ (other cells or the same cells coexpressing both markers) according to the present invention serves to discriminate neoplastic or preneoplastic lesions from metaplasias.

HPV encoded gene-products as used in the context of the present invention shall be any mRNA transcribed from a gene of the HPV genome or any polypeptide translated from such an mRNA. HPV gene-products suitable for the method according to the present invention are gene-products encoded by the E6, E7, L1 and L2 genes. In one especially preferred embodiment of the present invention the HPV gene-product is encoded by the HPV E2 gene.

HPV herein means human papilloma virus. HPV as used herein shall comprise any high risk subtype of HPV. In a preferred embodiment of the present invention the HPV subtype is a cancer associated HPV subtype such as e.g. HPV 16, 18, 31, 33, 35, 39, 45, 51, 52, 56 and 58. In an especially preferred embodiment the HPV high risk subtypes are HPV 16, 18, 39 or HPV 45. Subtyping of the HPV shall comprise any method suitable of the determination of the particular HPV subtype present in a biological sample.

The method for detection of the level of the HPV encoded gene-products according to the present invention is any method, which is suited to detect very small amounts of specific biological molecules in biological samples. The detection reaction according to the present invention is a detection either on the level of nucleic acids or on the level of polypeptides.

The HPV gene-products may be detected using reagents that specifically recognise these molecules. The detection reaction for the HPV gene-products may comprise one or more reactions with detecting agents either recognizing the initial marker molecules or recognizing the prior molecules used to recognize other molecules.

The detection reaction further may comprise a reporter reaction indicating the presence or absence and/or the level of the HPV gene-products. The reporter reaction may be for example a reaction producing a coloured compound, a bioluminescence reaction, a fluorescence reaction, generally a radiation emitting reaction etc.

In a preferred embodiment, different marker molecules may be recognized by agents, that produce different reporter signals, so that the signals referring to marker molecules could be distinguished. In one preferred embodiment of the invention the detection of the expression of high risk HPV gene-products is carried out simultaneously with the detection of the overexpression of $p16^{INK4a}$. In this case the reporter reaction may for example employ different fluorescent labels for the different molecules detected.

Applicable formats for the detection reaction according to the present invention may be, blotting techniques, such as Western-Blot, Southern-blot, Northern-blot. The blotting techniques are known to those of ordinary skill in the art and may be performed for example as electro-blots, semidry-blots, vacuum-blots or dot-blots. Amplification reaction may also be applicable for the detection of e.g. nucleic acid molecules.

In one preferred embodiment of the invention the detection of the level of HPV gene-products is carried out by detection of the respective mRNA or fragments thereof present in the sample. The means for detection of nucleic acid molecules are known to those skilled in the art. The procedure for the detection of nucleic acids can for example be carried out by a binding reaction of the molecule to be detected to complementary nucleic acid probes, proteins with binding specificity for the nucleic acids or any other entities specifically recognizing and binding to said nucleic acids.

This method can be performed as well in vitro as directly in situ for example in the course of a detecting staining reaction. Another way of detecting the HPV mRNAs in a sample performed in the method according to the present invention is an amplification reaction of nucleic acids, which can be carried out in a quantitative manner such as for example the polymerase chain reaction. In a preferred embodiment of the present invention, real time RT PCR is used to quantify the level of HPV mRNA in samples of tumors.

In another preferred embodiment of the invention, the detection of the level of HPV gene-products is carried out by determining the level of expression of a protein. The determination of the HPV gene-product on the protein level can, for example, be carried out in a reaction comprising a binding agent specific for the detection of the particular HPV polypeptide.

The binding agents can be used in many different detection techniques for example in western-blot, ELISA or immuno-precipitation. Generally polypeptide binding agent based detection can be carried out as well in vitro as directly in situ for example in the course of an immuno-histochemical staining reaction. Any other method for determining the amount of particular polypeptides in biological samples can be used according to the present invention.

Binding agents as used in the context of the present invention for the detection of the level of either HPV polypeptides or $p16^{INK4a}$ polypeptides may comprise antibodies and antigen-binding fragments, bifunctional hybrid antibodies, peptidomimetics containing minimal antigen-binding epitopes etc.

An antibody or antigen-binding agent is said to react specifically, if it reacts at a detectable level with a protein disclosed herein, and does not significantly react with other proteins. The antibodies according to the present invention may be monoclonal or polyclonal antibodies. As used herein, the term antibody or monoclonal antibody is meant to include intact molecules as well as antibody fragments. Moreover, antibodies of the present invention include chimeric, single chain, and humanized antibodies.

According to the present invention binding agents may be used isolated or in combination. By means of combination it is possible to achieve a higher degree of sensitivity. The term antibody, preferably, relates to antibodies which consist essentially of pooled monoclonal antibodies with different epitopic specificities, as well as distinct monoclonal antibody preparations.

Monoclonal antibodies are made from antigen containing fragments of the polypeptide of the invention using any of a variety of techniques known to those of ordinary skill in the art; see, e.g., Harlow and Lane, Antibodies: A Laboratory Manual, Cold Spring Harbour Laboratory, 1988. In one such technique, an immunogen comprising the antigenic polypeptide or a synthetic part thereof is initially injected into any of a wide variety of mammals (e.g., mice, rats, rabbits, sheep and goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

The methods used for the detection of the presence or absence of overexpression of $p16^{INK4a}$ according to the present invention are the same methods mentioned above for the detection of HPV gene-products.

The HPV gene-products may according to the present invention be detected simultaneously with the presence or absence of the overexpression of $p16^{INK4a}$. In this context simultaneously according to the present invention shall mean either literally at the same instant or within the same testing procedure, whereby the single detection steps are temporarily consecutive.

A sample according to the method of the present invention may comprise any sample comprising cells of anogenital origin. Samples may comprise e.g. secretions, smears, body fluids, and cell-samples.

In one embodiment of the present invention, samples comprise cells of the uterine cervix. In a preferred embodiment of the present invention the sample of cervical cells may be prepared according to a classical Pap smear. In a further preferred embodiment of the present invention, the sample may be prepared as a monolayer or thin layer preparation of the cytological specimen.

Preparation of a sample may comprise e.g. obtaining a sample of a tissue, of a body fluid, of cells from a patient. According to the present invention, preparation of the sample may also comprise several steps of further preparations of the sample, such as preparation of dissections, spreading or applying the cells to be examined onto microscopic slides, preparation of tissue arrays, isolation of polypeptides or nucleic acids, preparation of solid phase fixed peptides or nucleic acids or preparation of beads, membranes or slides to which the molecules to be determined are coupled covalently or non-covalently.

The neoplastic lesions to which the method according to the present invention may be applied comprise any anogenital lesion, which is characterized by the overexpression of $p16^{INK4a}$, which furthermore shows expression of HPV gene-products. In one preferred embodiment of the present invention the anogenital lesion is a lesion of the uterine cervix.

Another aspect of the present invention is a testing kit for performing the method according to the present invention. The kit may be for example a diagnostic kit or a research kit.

A kit according to the present invention comprises at least an agent suitable for detecting the HPV gene-products and an agent suitable for the detection of the presence or absence of the overexpression of $p16^{INK4a}$.

Thus a kit according to present invention may comprise:
a) reagents for the detection of the HPV gene-products
b) reagents for the detection of the $p16^{INK4a}$ overexpression
c) reagents and buffers commonly used for carrying out the detection reaction, such as buffers, detection-markers, carrier substances and others
d) a $p16^{INK4a}$ sample for carrying out a positive control reaction
e) a HPV gene-product sample for carrying out a positive control reaction The reagents for the detection of the HPV gene-products and/or $p16^{INK4a}$ may include any agent capable of binding to the HPV gene-products and/or $p16^{INK4a}$ molecule. Such reagents may include proteins, polypeptides, nucleic acids, peptide nucleic acids, glycoproteins, proteoglycans, polysaccharides or lipids.

The HPV gene-product and/or $p16^{INK4a}$ sample for carrying out a positive control may comprise for example nucleic acids in applicable form, such as solution or salt, peptides in applicable form, tissue section samples or positive cells.

In a preferred embodiment of the invention, the detection of the HPV gene-products and/or $p16^{INK4a}$ is carried out on the level of polypeptides. In this embodiment, the binding agents may be for example antibodies specific for the HPV gene-products or $p16^{INK4a}$ or fragments thereof.

In an other embodiment of the test kit, the detection of the HPV gene-products and/or $p16^{INK4a}$ is carried out on the nucleic acid level. In this embodiment of the invention, the reagent for the detection may be, for example, a nucleic acid probe or a primer reverse-complementary to said HPV gene-product and/or $p16^{INK4a}$ nucleic acids.

The present invention provides a method for the discrimination of neoplastic and preneoplastic anogenital lesion identifiable by assessment of the overexpression of $p16^{INK4a}$ from metaplastic cells, which detectably express $p16^{INK4a}$ in the course of cytological testing procedures. The method is based on the detection of expressed gene-products of high risk HPV. It turned out, that high risk HPV gene-products expressed in high levels in the early stages of neoplasias and in preneoplasias are suitable for this discrimination. This is due to the fact that the percentage of cells in a biological sample in early stages of neoplasias overexpressing $p16^{INK4a}$ renders a level of $p16^{INK4a}$ molecules, that there remains the possibility, that the level recurs to metaplastic rather than neoplastic cells. Thus the problem to be solved was to provide a method for discrimination between neoplastic and metaplastic cells especially in early stages of neoplasias, when cytological diagnostic methods based on the $p16^{INK4a}$ overexpression needs a further information for the identification of metaplastic cells.

Furthermore the present invention provides a kit for performing the method according to the present invention.

EXAMPLES

The following examples are given for the purpose of illustration only and are not intended to limit the scope of the invention disclosed herein.

Example 1: Immunochemical Detection of the Expression of HPV E2, L1 and $p16^{INK4a}$ in Samples of the Uterine Cervix Smears of the cervix uteri were immunocytochemically stained using antibodies specific for $p16^{INK4a}$, polyclonal antibodies specific for HPV L1 and polyclonal antibodies specific for HPV E2 protein.

For rehydration, the spray-fixed smears prepared on slides were incubated in fresh 50% EtOH on a rocking device. The PEG film produced by the fixation procedure was removed by intensive rinsing. The smears were rinsed in aqua bidest. Antigen Retrieval was carried out with 10 mM citrate buffer (pH 6.0). Then the slides were heated in a water bath for 40 min at 95° C., cooled down to RT for 20 minutes, transferred to washing buffer (PBS/0.1% Tween20) and finally surrounded with a lipid-pencil.

For inactivation of endogenous peroxidase, the samples were incubated with 3% $H_2O_2$ for 20 min at RT and afterwards washed in PBS/0.1% Tween20 for 5 min. The proteinblock was carried out with horse-serum (Vectastain®-Kit) (Dilute 1:50 with PBS/0.1% Tween20). The smears were incubate for 20 min at RT and then rinsed off carefully. Then blocking of non-specific binding of avidin—reagent was performed as follows: Samples were incubated with avidin blocking solution (ready-to-use/Vector) for 15 min at RT and then washed carefully with pipette. For blocking of non-specific binding of biotin-reagent the smears were incubated with biotin blocking solution (ready-to-use/Vector) for 15 min at RT and then rinsed off carefully.

Then follows incubation with a $p16^{INK4a}$ specific primary antibody or polyclonal antibodies directed against HPV E2 protein or polyclonal antibodies raised against high risk (HPV16) HPV L1 protein; the samples were incubated for 60 min at RT, washed in PBS/0.1% Tween20 for 5 min (two times) and afterwards incubated with a biotinylated Secondary Antibody (horse-anti-mouse-IgG) (Vectastain®-Kit/Dilute 1:200 in PBS/0.1% Tween20+Horse-Serum) for 30 min at RT and washed in PBS/0.1% Tween20 for 5 min (two times). Following an incubation with AB-Complex (Avidin-Biotin-HRP) (Vectastain®-Kit/Dilute 1:50 in PBS/0.1% Tween20) was performed for 30 min at RT followed by washing steps in PBS/0.1% Tween20 for 5 min (two times).

Signal detection was carried out with Substrate-Chromogen-Complex ($H_2O_2$/AEC) as follows: First the samples were incubate for 30 min at RT with the substrate-chromogen complex, then the reaction was stopped in aqua bidest. Finally, a counterstain with Mayers Hematoxylin was performed and the slides were mounted with Glycerin gelatin.

The microscopic examination of the slides revealed that cells immunoreactive with $p16^{INK4a}$ antibody together with cells immunoreactive with HPV E2 protein antibody can only be found in samples that were microscopically identified as samples of neoplastic lesions. Cells stained by the $p16^{INK4a}$ specific reaction, which were originating from metaplasias, were not stained by the reaction specific for the HPV E2 protein. The microscopic inspection of the HPV L1 stained slides showed that metaplastic cells were not immunoreactive with the antibodies directed against HPV L1 protein. Samples containing dysplastic cells in contrast comprise cells immunoreactive with HPV L1 antibody and cells immunoreactive with $p16^{INK4a}$ antibody. So in contrast to dysplasias, no cells in metaplasias were stained using the HPV L1 specific antibody.

The results show that the staining with reagents specific for HPV E2 or L1 allowed to discriminate $p16^{INK4a}$ overexpressing metaplasias from dysplasias.

Example 2: Detection of Cells Expressing HPV E2, HPV L1 or $p16^{INK4a}$ in Samples of the Uterine Cervix by In Situ Hybridization Smears of the uterine cervix are semi-quantitatively analysed for the mRNA level of $p16^{INK4a}$ and HPV E2 and L1 in an in-situ staining reaction. The staining reaction is performed as follows:

For rehydration, the spray-fixed smears prepared on slides are incubated in fresh 50% EtOH on a rocking device. The PEG film produced by the fixation procedure is removed by intensive rinsing. Then the smears are rinsed in aqua bidest. The smears are incubated with proteinase K (10 μg/ml in PBS) for 10 min at 37° C. Then the slides are transferred to washing buffer (PBS/0.1% Tween20) and finally surrounded with a lipid-pencil.

The hybridization mixture is prepared by mixing 50 μl of ready to use hybridization buffer (DAKO A/S, Glostrup, Denmark) with about 5-10 pmol of the probes. The probes are fluorescein-labelled oligonucleotides of sequences complementary to the respective mRNAs.

The hybridization mixture is heated to 95° C. and afterwards equilibrated to 37° C. After the boiling procedure, the smears are incubated with each 50 μl of the hybridization mixture for 4 hours at 42° C. The samples are washed in excess volumes of the wash buffers two times in 2×SSC at 37° C. for 15 min and once in 1×SSC at 37° C. for 15 min. Then the smears are rinsed two times at room temperature in 2×SSC. Following this washing procedure, the dissections are incubated for 30 min with blocking buffer (NEN, Blockingpugger) at room temperature, followed by 1 hour incubation with a 1:100 diluted (in Blocking buffer, see above) anti-Fluorescein-alkaline phosphatase (DAKO A/S). The smears are then washed 2 times in 1×PBS/0.1% Triton X-100 for 10 min at room temperature, followed by one wash step with 1×PBS, 50 mM $MgCl_2$ (pH 9.2) for 10 min at room temperature. Then the staining reaction is performed with NBT/BOP (Sigma) for 30 min to 2 hours at room temperature. The staining reaction is stopped by a short incubation with 1 mM EDTA in PBS. Finally the smears are dipped in $H_2O_{dest.}$ and embedded with AquaTex (Merck). Then the stained dissections can be analysed microscopically.

Microscopic analysis reveals that metaplasias comprise cells expressing $p16^{INK4a}$ but no cells expressing HPV L1 or E2 mRNA. In dysplastic lesions of the cervix uteri, cells expressing $p16^{INK4a}$ and cells expressing HPV L1 and HPV E2 mRNAs can be found.

This result indicates that the method according to the present invention may be used for the discrimination of metaplasias and neoplastic lesions.

Example 3: Immunocytochemical Detection of the Expression of HPV E7, and $p16^{INK4a}$ in Samples of the Uterine Cervix ThinPrep® thin layers of smears of the cervix uteri were immunocytochemically stained using antibodies specific for $p16^{INK4a}$ and monoclonal antibodies specific for HPV E7 protein.

For rehydration, the spray-fixed smears prepared on slides were incubated in fresh 50% EtOH on a rocking device. The PEG film produced by the fixation procedure was removed by intensive rinsing. Then the smears were rinsed in aqua bidest. Antigen Retrieval was carried out with 10 mM citrate buffer (pH 6.0). Thereafter, the slides were heated in a water bath for 40 min at 95-98° C., cooled down to RT for 20 minutes, transferred to washing buffer (Dakocytomation, S3006) and finally surrounded with a lipid-pencil.

For inactivation of endogenous peroxidase, the samples were incubated with 3% $H_2O_2$ (Dakocytomation; S2023) for 5 min at RT and afterwards washed in wash buffer (Dakocytomation, S3006) for 5 min, then followed by incubation with a $p16^{INK4a}$ specific primary antibody or monoclonal antibodies directed against high risk (HPV16) E7 protein. The samples were incubated for 30 min at RT, washed in wash buffer for 5 min and afterwards incubated with the EnVision system (Dakocytomation, K4001), consisting of goat anti-mouse antibodies conjugated to a dextran polymer and peroxidase enzymes, for 30 min at RT and washed in wash buffer for 5 min (three times).

Signal detection was carried out with Substrate-Chromogen-Complex (DAB+, Dakocytomation, K3468) by incubation for 10 min at RT. Then the reaction was stopped in aqua dest. Finally a counterstain with Mayers Hematoxylin was performed and the slides were mounted with Faramount (DakoCytomation, S3025).

The microscopic examination of the slides revealed, that cells immunoreactive with $p16^{INK4a}$ antibody together with cells immunoreactive with HPV E7 protein antibody can only be found in samples, that were microscopically identified as samples of neoplastic lesions. Cells stained by the $p16^{INK4a}$ specific reaction, which were originating from metaplasias, were not stained by the reaction specific for the HPV E7 protein.

Figure 1:
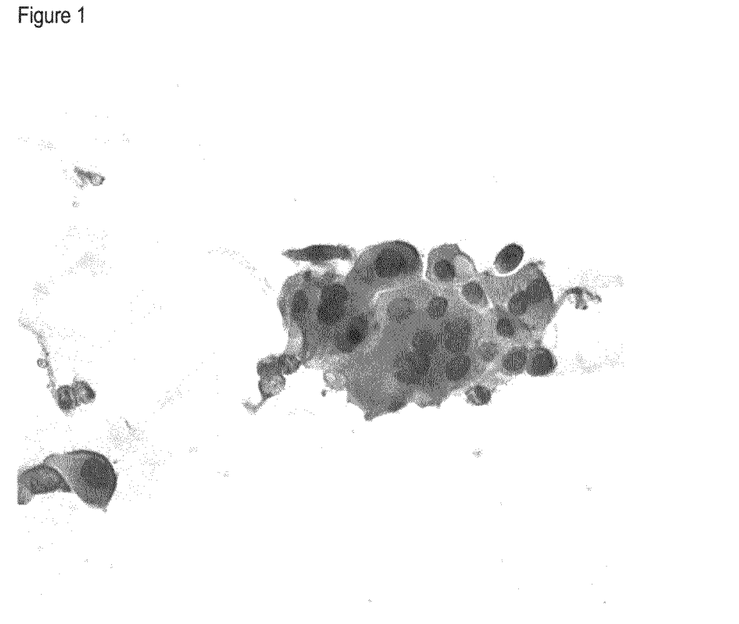
FIG. 1 shows metaplastic cells immunochemically stained with an antibody specific for $p16^{INK4a}$.
Figure 2:
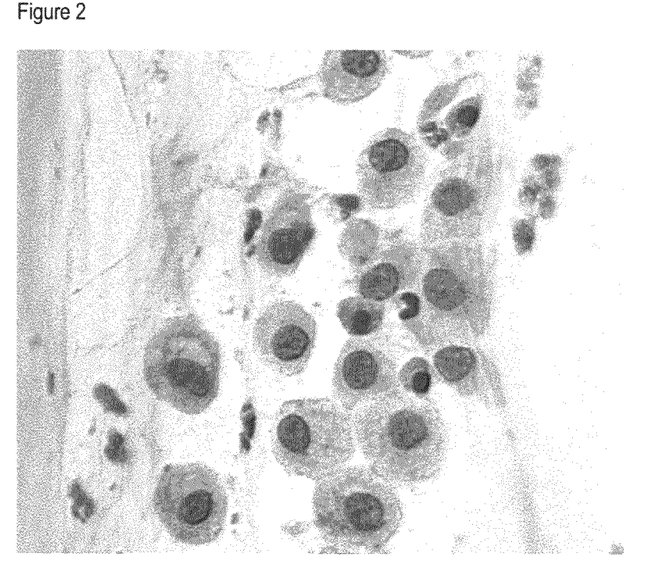
FIG. 2 shows metaplastic cells immunochemically stained with an antibody specific for HPV E2.
Figure 3:
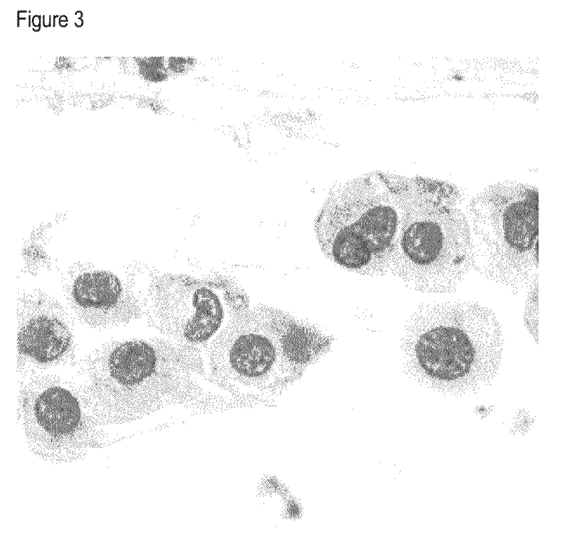
FIG. 3 shows metaplastic cells immunochemically stained with an antibody specific for HPV L1.
Figure 4:
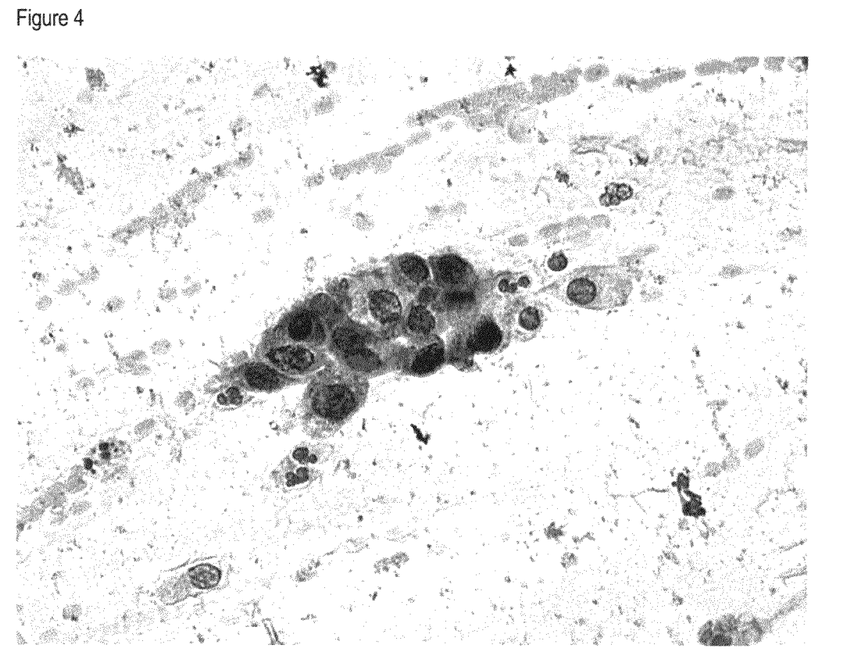
FIG. 4 shows dysplastic cells immunochemically stained with an antibody specific for $p16^{INK4a}$. For experimental details see Example 1; the cells clearly react with the antibodies against $p16^{INK4a}$.
Figure 5:
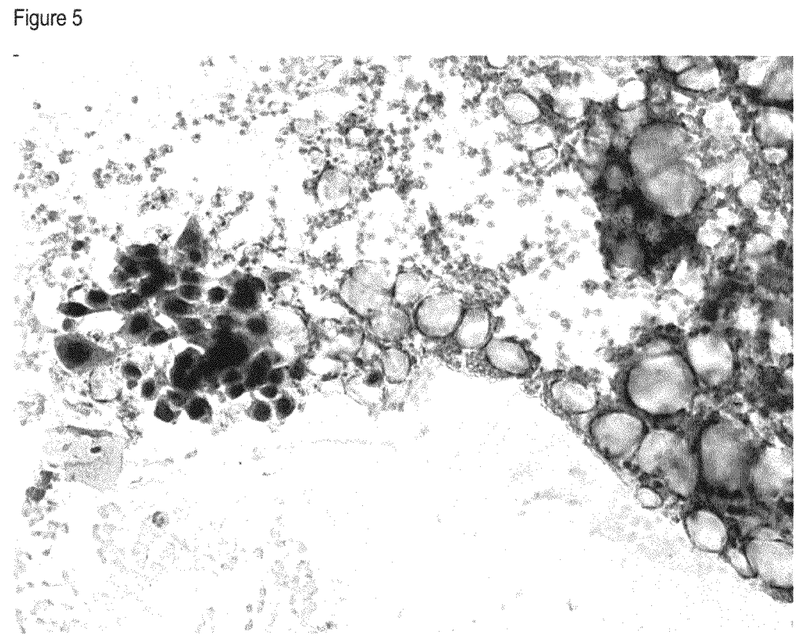
FIG. 5 shows dysplastic cells immunochemically stained with an antibody specific for HPV E2. For experimental details see Example 1; the cells show clear immunoreactivity with the polyclonal antibodies directed against HPV E2 protein.
Figure 6:
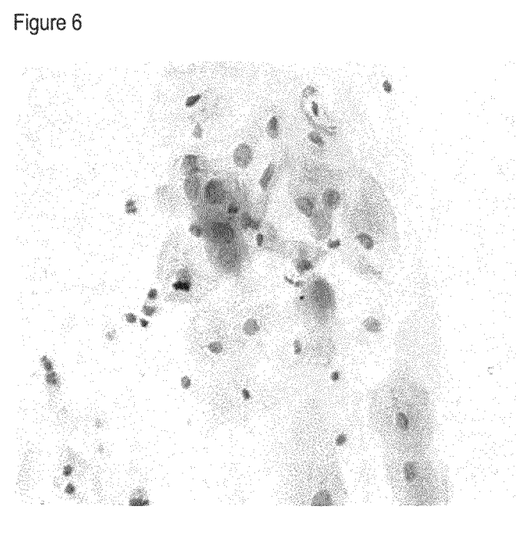
FIG. 6 shows dysplastic cells immunochemically stained with an antibody specific for HPV L1. For experimental details see Example 1; the cells show clear immunoreactivity with the polyclonal antibodies directed against HPV L1 protein.
Figure 7:
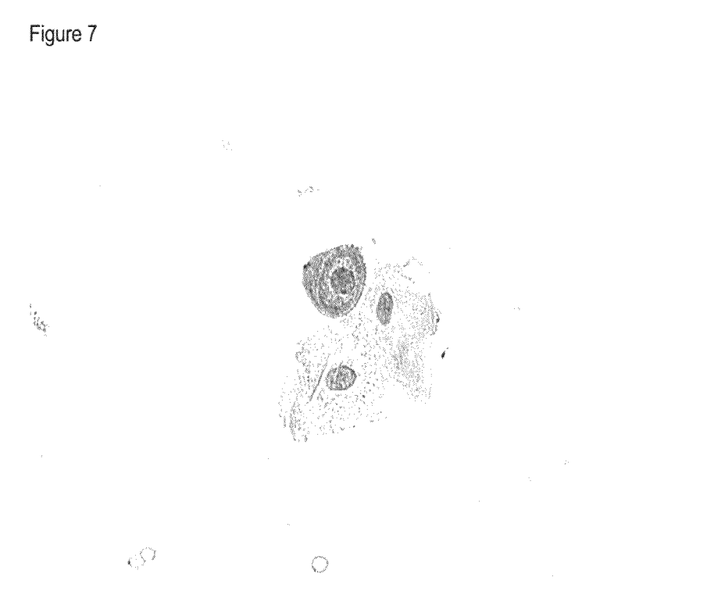
FIG. 7 shows metaplastic cells immunochemically stained with an antibody specific for $p16^{INK4a}$. For experimental details see Example 3; the cells clearly react with the antibodies against $p16^{INK4a}$.
Figure 8:
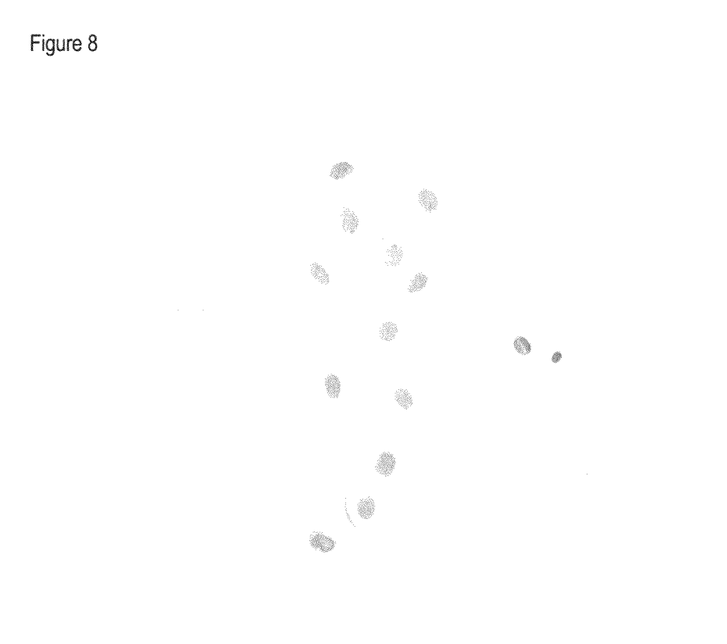
FIG. 8 shows metaplastic cells immunochemically stained with an antibody specific for HPV E7. For experimental details see Example 3; the cells do not show immunoreactivity with the monoclonal antibodies directed against HPV E7 protein.
Figure 9:
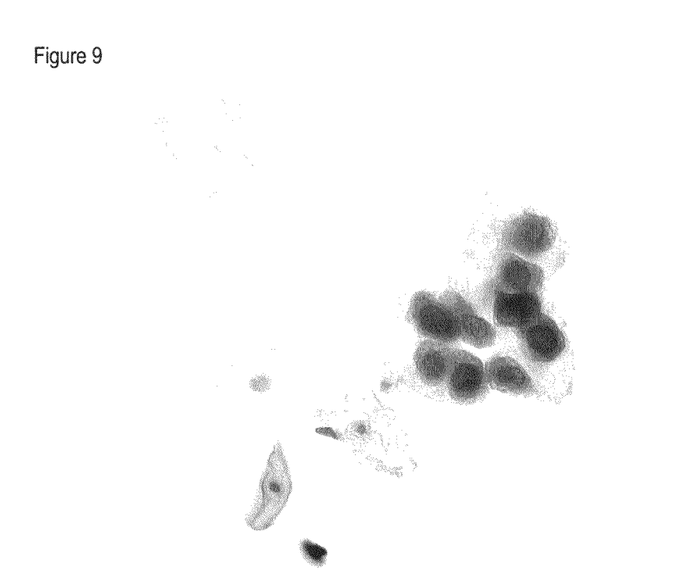
FIG. 9 shows dysplastic cells immunochemically stained with an antibody specific for $p16^{INK4a}$. For experimental details see Example 3; the cells clearly react with the antibodies against $p16^{INK4a}$.
Figure 10:
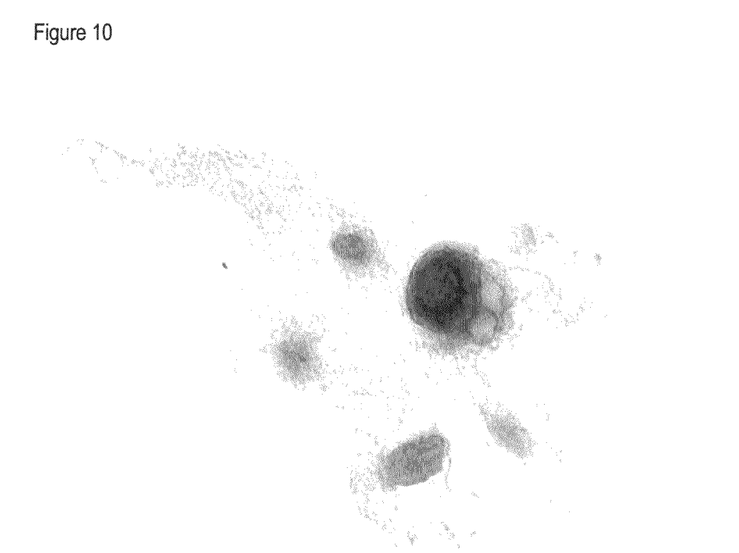
FIG. 10 shows dysplastic cells immunochemically stained with an antibody specific for HPV E7. For experimental details see Example 3; the cells clearly react with the antibodies against HPV E7 protein.
Figure 11:
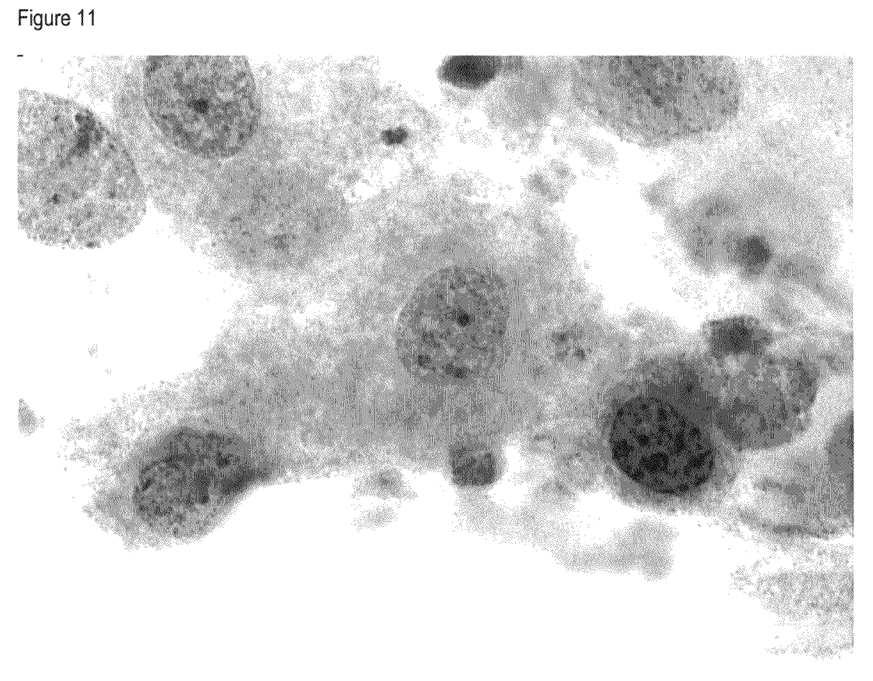
FIG. 11 shows dysplastic cells immunochemically double stained with antibodies specific for HPV E7 and antibodies specific for $p16^{INK4a}$. For experimental details see Example 3; the cells clearly react with the antibodies against both HPV E7 and $p16^{INK4a}$ proteins.

To validate the results given herein, a double staining of cytological specimens was performed using a FITC-labelled HPV E7 antibody (antibody as given above) in combination with the $p16^{INK4a}$ antibody as used above. The staining was performed as given above adapted to a double staining procedure. The necessary variations are known to those of skill in the art.

In double stained specimens, no double stained metaplastic cells were found; in contrast dysplastic cells showed double staining for p16$^{INK4a}$ and HPV E7 protein.

The results show that the staining with reagents specific for HPV E7 allows to discriminate p16$^{INK4a}$ overexpressing metaplasias from dysplasias.

What is claimed is:

1. A method for screening a uterine cervical cytology sample determined to over-express a p16$^{INK4a}$ gene product, comprising:
   (a) obtaining at least one slide having the uterine cervical cytology sample deposited thereon; and
   (b) either:
       (b1) in situ hybridization staining the uterine cervical cytology sample with a labelled oligonucleotide probe that is complementary to a mRNA encoded by a high risk HPV (hr-HPV) gene selected from the group consisting of HPV E7 gene, HPV E2 gene, HPV E6 gene, HPV L1 gene, and HPV L2 gene, wherein the in situ hybridization stain deposits an agent that generates a reporter signal, or
       (b2) immunocytochemically staining the uterine cervical cytology sample with a primary antibody that is immunospecific for a protein encoded by a hr-HPV gene selected from the group consisting of HPV E7 gene, HPV E2 gene, HPV E6 gene, HPV L1 gene, and HPV L2 gene, wherein the immunocytochemical stain deposits the agent that generates the reporter signal.

2. The method according to claim 1, wherein the hr-HPV gene is the HPV E7 gene.

3. The method according to claim 1, wherein the hr-HPV gene is the HPV E2 gene or the HPV E6 gene.

4. The method according to claim 1, wherein the hr-HPV gene is the HPV L1 gene or the HPV L2 gene.

5. The method of claim 1, wherein the agent generating the reporter signal is a fluorescent label.

6. The method of claim 1, wherein the agent generating the reporter signal is a colored compound.

7. The method according to claim 6, wherein the colored compound that generates the first reporter signal and the second reporter signal is diaminobenzidine.

8. A method of preparing a uterine cervical cytology sample for microscopic evaluation, said method comprising:
   (a) obtaining a slide having the uterine cervical cytology sample deposited thereon;
   (b) staining the uterine cervical sample on the slide by:
       (b1) either immunocytochemically staining human p16$^{INK4a}$ protein with an agent that generates a first reporter signal or, in situ hybridization staining a mRNA encoding human p16$^{INK4a}$ protein with the agent that generates the first reporter signal; and
       (b2) either immunocytochemically staining a protein encoded by a high risk HPV (hr-HPV) gene with an agent that generates a second reporter signal, or in situ hybridization staining a mRNA encoded by the hr-HPV gene with the agent that generates the second reporter signal, wherein the hr-HPV gene is selected from the group consisting of HPV E7 gene, HPV E2 gene, HPV E6 gene, HPV L1 gene, and HPV L2 gene, and wherein the first reporter signal is distinguishable from the second reporter signal.

9. The method of claim 8, wherein the agent generating the first reporter signal and the agent generating the second reporter signal are different fluorescent labels or different colored compounds.

10. The method according to claim 8, wherein the hr-HPV gene is the HPV E7 gene.

11. The method according to claim 8, wherein the hr-HPV gene is the HPV E2 gene or the HPV E6 gene.

12. The method according to claim 1, wherein the hr-HPV gene is the HPV L1 gene or the HPV L2 gene.

13. A method of preparing a uterine cervical cytology sample for microscopic evaluation, said method comprising:
   (a) obtaining at least two slides having the uterine cervical cytology sample deposited thereon;
   (b) staining at least one of the slides by either immunocytochemically staining human p16$^{INK4a}$ protein with an agent that generates a first reporter signal, or in situ hybridization staining a mRNA encoding human p16$^{INK4a}$ protein with the agent that generates the first reporter signal; and
   (c) staining at least another of the slides by either immunocytochemically staining a protein encoded by a high risk HPV (hr-HPV) gene with an agent that generates a second reporter signal, or in situ hybridization staining a mRNA encoded by the hr-HPV gene with the agent that generates the second reporter signal, and wherein the hr-HPV gene is selected from the group consisting of HPV E7 gene, HPV E2 gene, HPV E6 gene, HPV L1 gene, and HPV L2 gene.

14. The method of claim 13, wherein the agent generating the first reporter signal and the agent generating the second reporter signal are fluorescent labels or colored compounds.

15. The method according to claim 13, wherein the hr-HPV gene is the HPV E7 gene.

16. The method according to claim 13, wherein the hr-HPV gene is the HPV E2 gene or the HPV E6 gene.

17. The method according to claim 13, wherein the hr-HPV gene is the HPV L1 gene or the HPV L2 gene.

* * * * *